United States Patent
Zhang et al.

(10) Patent No.: US 9,186,334 B2
(45) Date of Patent: *Nov. 17, 2015

(54) HEAT ASSISTED LIDOCAINE AND TETRACAINE FOR TRANSDERMAL ANALGESIA

(75) Inventors: Jie Zhang, Salt Lake City, UT (US); Robert Lippert, Park City, UT (US)

(73) Assignee: Nuvo Research Inc., Mississauga, Ontario (CA)

(*) Notice: Subject to any disclaimer, the term of this patent is extended or adjusted under 35 U.S.C. 154(b) by 0 days.

This patent is subject to a terminal disclaimer.

(21) Appl. No.: 13/049,650

(22) Filed: Mar. 16, 2011

(65) Prior Publication Data

US 2012/0065259 A1     Mar. 15, 2012

Related U.S. Application Data

(63) Continuation-in-part of application No. 12/773,239, filed on May 4, 2010.

(60) Provisional application No. 61/175,181, filed on May 4, 2009.

(51) Int. Cl.

| A61K 31/24 | (2006.01) |
|---|---|
| A61K 9/70 | (2006.01) |
| A61F 7/02 | (2006.01) |
| A61F 7/03 | (2006.01) |
| A61K 31/167 | (2006.01) |
| A61K 31/245 | (2006.01) |
| A61F 7/00 | (2006.01) |

(52) U.S. Cl.
CPC .............. *A61K 9/7023* (2013.01); *A61F 7/02* (2013.01); *A61F 7/034* (2013.01); *A61K 31/167* (2013.01); *A61K 31/245* (2013.01); *A61F 2007/0071* (2013.01); *A61F 2007/0226* (2013.01); *A61F 2007/0257* (2013.01); *A61F 2007/0261* (2013.01); *A61F 2007/0292* (2013.01)

(58) Field of Classification Search
None
See application file for complete search history.

(56) References Cited

U.S. PATENT DOCUMENTS

| 3,929,131 A | 12/1975 | Hardwick |
|---|---|---|
| 4,210,670 A | 7/1980 | Cooke |
| 4,230,105 A | 10/1980 | Harwood |
| 4,286,592 A | 9/1981 | Chandrasekaran |
| 4,529,601 A | 7/1985 | Broberg et al. |
| 4,685,911 A | 8/1987 | Konno et al. |
| 4,693,706 A | 9/1987 | Ennis, III |
| 4,747,841 A | 5/1988 | Kuratomi et al. |
| 4,830,855 A | 5/1989 | Stewart |
| 4,879,119 A | 11/1989 | Konno et al. |
| 4,898,592 A | 2/1990 | Latzke et al. |
| 4,911,707 A | 3/1990 | Heiber et al. |
| 4,913,957 A | 4/1990 | Strack et al. |
| 4,963,360 A | 10/1990 | Argaud |
| 4,994,049 A | 2/1991 | Latzke et al. |
| 5,108,710 A | 4/1992 | Little et al. |
| 5,114,411 A | 5/1992 | Haber et al. |
| 5,128,137 A | 7/1992 | Muller et al. |
| 5,147,339 A | 9/1992 | Sundstrom |
| 5,213,129 A | 5/1993 | Someah et al. |
| 5,217,718 A | 6/1993 | Colle et al. |
| 5,229,133 A | 7/1993 | Wright et al. |
| 5,276,032 A | 1/1994 | King et al. |
| 5,279,594 A | 1/1994 | Jackson |
| 5,298,257 A | 3/1994 | Bannon et al. |
| 5,329,976 A | 7/1994 | Haber et al. |
| 5,330,452 A | 7/1994 | Zook |
| 5,364,350 A | 11/1994 | Dittmann |
| 5,378,730 A | 1/1995 | Lee et al. |
| 5,534,021 A | 7/1996 | Dvoretzky et al. |
| 5,580,573 A | 12/1996 | Kydonieus et al. |
| 5,626,571 A | 5/1997 | Young et al. |
| 5,651,768 A | 7/1997 | Sibalis |
| 5,658,583 A | 8/1997 | Zhang et al. |
| 5,662,624 A | 9/1997 | Sundstrom et al. |
| 5,679,373 A | 10/1997 | Wick et al. |
| 5,728,057 A | 3/1998 | Ouellette et al. |
| 5,728,058 A | 3/1998 | Ouellette et al. |

(Continued)

FOREIGN PATENT DOCUMENTS

| CA | 2228137 | 2/1997 |
|---|---|---|
| CA | 2408585 | 2/1997 |

(Continued)

OTHER PUBLICATIONS

Argoff (Curr Pain and Headache Reports 6:375-378, 2002).*
Ohzeki et al (Yakugaku Zasshi 128:611-616, 2008).*
Yap (Ann Acad Med Singapore 36:43-48, 2007).*
Tadicherla et al (Therapeutics and Clin Risk Management 2:99-113, 2006).*
Nalamachu et al (MedGenMed 8:33, 2006).*
Burch (OsteoArthritis and Cartilage 12:253-255, 2004).*

(Continued)

*Primary Examiner* — Craig Ricci
(74) *Attorney, Agent, or Firm* — Thorpe North & Western LLP

(57) ABSTRACT

The present disclosure is drawn to methods for treating various types of pain, including pain associated nerve entrapment, neuroma, headaches, connective tissue, arthritis, injury, and/or overuse. Specifically, the method includes the application of an analgesic system to a skin surface of a subject experiencing the pain and maintaining the analgesic system on the skin surface for an application period of at least 30 minutes. Following the application period the analgesic system can be removed and the subject being treated continues to experience reduction of pain for a period of 2 to 10, or even 4 to 12 hours after removal of the analgesic system. The analgesic system applied to the skin surface can include a heating component and a local anesthetic formulation.

35 Claims, 1 Drawing Sheet

(56) References Cited

U.S. PATENT DOCUMENTS

| | | | |
|---|---|---|---|
| 5,728,146 A | 3/1998 | Burkett et al. |
| 5,730,721 A | 3/1998 | Hyatt et al. |
| 5,733,255 A | 3/1998 | Dinh et al. |
| 5,735,889 A | 4/1998 | Burkett et al. |
| 5,741,318 A | 4/1998 | Ouellette et al. |
| 5,776,952 A | 7/1998 | Liedtke |
| 5,837,005 A | 11/1998 | Viltro et al. |
| 5,840,755 A | 11/1998 | Liedtke |
| 5,860,945 A | 1/1999 | Cramer et al. |
| 5,904,710 A | 5/1999 | Davis et al. |
| 5,906,637 A | 5/1999 | Davis et al. |
| 5,906,830 A | 5/1999 | Farinas et al. |
| 5,919,479 A | 7/1999 | Zhang et al. |
| 5,925,072 A | 7/1999 | Cramer et al. |
| 5,980,562 A | 11/1999 | Ouellette et al. |
| 5,984,995 A | 11/1999 | White |
| 5,993,836 A | 11/1999 | Castillo |
| 6,019,782 A | 2/2000 | Davis et al. |
| 6,020,040 A | 2/2000 | Cramer et al. |
| 6,024,761 A | 2/2000 | Barone et al. |
| 6,042,673 A | 3/2000 | Johnson et al. |
| 6,048,326 A | 4/2000 | Davis et al. |
| 6,245,347 B1 | 6/2001 | Zhang et al. |
| 6,261,595 B1 | 7/2001 | Stanley et al. |
| 6,284,266 B1 | 9/2001 | Zhang et al. |
| 6,303,142 B1 | 10/2001 | Zhang et al. |
| 6,306,431 B1 | 10/2001 | Zhang et al. |
| 6,340,472 B1 | 1/2002 | Zhang et al. |
| 6,453,648 B1 | 9/2002 | Zhang et al. |
| 6,465,006 B1 | 10/2002 | Zhang et al. |
| 6,465,709 B1 * | 10/2002 | Sun et al. ............... 602/48 |
| 6,488,959 B2 | 12/2002 | Stanley et al. |
| 6,528,086 B2 | 3/2003 | Zhang |
| 6,546,281 B1 | 4/2003 | Zhang et al. |
| 6,613,350 B1 | 9/2003 | Zhang et al. |
| 6,726,673 B1 | 4/2004 | Zhang et al. |
| 6,756,053 B2 | 6/2004 | Zhang et al. |
| 6,756,426 B2 | 6/2004 | Brother et al. |
| 6,780,426 B2 | 8/2004 | Zhang et al. |
| 6,890,553 B1 | 5/2005 | Sun et al. |
| 6,929,131 B1 | 8/2005 | Landi |
| 6,955,819 B2 | 10/2005 | Zhang et al. |
| 7,718,674 B2 | 5/2010 | Aberg |
| 2001/0037104 A1 | 11/2001 | Zhang et al. |
| 2002/0119118 A1 | 8/2002 | Fong et al. |
| 2003/0012830 A1 | 1/2003 | Small |
| 2003/0138505 A1 | 7/2003 | Fischer et al. |
| 2005/0209319 A1 | 9/2005 | Cundy |
| 2006/0078600 A1 | 4/2006 | Muller |
| 2006/0147510 A1 | 7/2006 | Galer |
| 2007/0059351 A1 | 3/2007 | Murrell et al. |
| 2007/0068508 A1 * | 3/2007 | York-Leung Wong .. 126/263.02 |
| 2007/0189978 A1 | 8/2007 | Zhang et al. |
| 2007/0196323 A1 | 8/2007 | Zhang et al. |
| 2007/0196458 A1 | 8/2007 | Zhang et al. |
| 2008/0021051 A1 | 1/2008 | Wilson |
| 2011/0015229 A1 | 1/2011 | Zhang et al. |
| 2011/0086913 A1 | 4/2011 | Zhang et al. |
| 2011/0112189 A1 | 5/2011 | Zhang |

FOREIGN PATENT DOCUMENTS

| | | |
|---|---|---|
| EP | 0304227 | 8/1988 |
| EP | 2205496 | 4/2009 |
| EP | 2163956 | 3/2010 |
| GB | 2163956 | 3/1986 |
| GB | 2205496 | 12/1988 |
| JP | H05-170644 | 9/1993 |
| JP | H11-510075 A | 9/1999 |
| JP | 2002/525172 A | 8/2002 |
| JP | 2003/510259 A | 3/2003 |
| JP | 2009174243 | 8/2009 |
| WO | WO 85/02124 | 5/1985 |
| WO | WO 88/09169 | 12/1988 |
| WO | WO 93/07842 | 4/1993 |
| WO | WO 93/07870 | 4/1993 |
| WO | WO 97/01310 | 1/1997 |
| WO | WO 97/01311 | 1/1997 |
| WO | WO 97/01312 | 1/1997 |
| WO | WO 97/01313 | 1/1997 |
| WO | WO 97/04728 | 2/1997 |
| WO | WO 9704728 | 2/1997 |
| WO | WO 97/36968 | 3/1997 |
| WO | WO 97/49361 | 12/1997 |
| WO | WO 98/00118 | 1/1998 |
| WO | WO 98/28021 | 7/1998 |
| WO | WO 98/28024 | 7/1998 |
| WO | WO 98/29063 | 7/1998 |
| WO | WO 98/29064 | 7/1998 |
| WO | WO 98/29065 | 7/1998 |
| WO | WO 98/29066 | 7/1998 |
| WO | WO 98/29067 | 7/1998 |
| WO | WO 99/09917 | 3/1999 |
| WO | WO 99/09918 | 3/1999 |
| WO | WO 00/18339 | 4/2000 |
| WO | WO 01/22907 | 4/2001 |
| WO | WO 2007/070679 | 6/2007 |
| WO | WO 2008/106220 A1 | 9/2008 |
| WO | WO 2008/150995 | 12/2008 |
| WO | WO 2009/053572 | 4/2009 |
| WO | WO 2010080831 | 7/2010 |
| WO | WO 2010/114973 A1 | 10/2010 |
| WO | WO 2010/129542 | 11/2010 |
| WO | WO 2011/028542 | 3/2011 |

OTHER PUBLICATIONS

PCT Application PCT/US10/33538; filed May 4, 2010; Jie Zhang.
PCT Application PCT/US10/29580; filed Apr. 1, 2010; Jie Zhang.
PCT Application PCT/US10/46523; filed Aug. 24, 2010; Jie Zhang.
Moghtaderi et al.; EMLA Cream for Carpal Tunnel Syndrome: How it Compares with Steroid Injection; Electomyogr Clin Neurophysiol; Sep.-Oct. 2009; vol. 49 No. 6-7; pp. 287-289 (abstract only).
Nalamachu et al.; A Comparison of the Lidocaine Patch 5% vs Naproxen 500rnp Twice Daily for the Relief of Pain Associated with Carpal Tunnel Syndrome: a 6-Week, Randomized, Parallel-Group Study; MedGenMed; Aug. 2006; vol. 8 No. 3.
Nalamach et al.; Lidocaine Patch 5 for Carpal Tunnel Syndrome: How it Compares with Injections: a Pilot Study; J Fam Pract; Mar. 2006; vol. 55 No. 3; pp. 209-214.
Wallace et al.; Evaluation of the Depth and Duration of Anesthesia From Heated LidocaineTetracain (Synera)patches Compared with Placebo Patches Applied to Healthy Adult Volunteers; Regional Anesthesia and Pain Medicine; Nov.-Dec. 2010; vol. 35, No. 6; pp. 507-513.
Young et al; What's New in Topical Anesthesia; Clinical Pediatric Emergency Medicine; Dec. 3, 2007; pp. 232-239; vol. 8, No. 4.
Cada et al; Lidocaine/Tetracain Patch; Hospital Pharmacy; 2006; pp. 265-273; vol. 41, No. 3.
Ohzeki et al; Local Anesthetic Cream Prepared from Lidocaine-Tetracaine Antectic Mexture; Yakugaku Zasshi; 2008; pp. 611-616; vol. 128.
Argoff et al; A review of the Use of Topical Analgesics for Myofascial Pain; Curr Pain and Headache Reports; 2002; pp. 375-378, vol. 6.
Croxtall, Lidocaine/tetracaine medicated plaster: in minor dermatological and needle puncture procedures. Drugs. 2010; 70:2113-2120.
Shainhouse, Topical anesthetics: physiology, formulations, and novel delivery systems. Am J. Drug Delivery. 2004; 2:89-99.
Shaikh, The influence of a eutectic mixture of lidocaine and prilocaine on minor surgical procedures: a randomized controlled double-blind trial. Dermatol Surg. 2009; 35:948-951.
Tang, Study on the efficacy of ELA-MAX (4% liposomal lidocaine) compared with EMLA cream (eutectic mixture of local anesthetics) using thermosensory threshold analysis in adult volunteers. J Dermatol Treat. 2004; 15:84-87.
Sawyer, Heated lidocaine/tetracaine patch (Synera, Rapydan) compared with lidocaine/prilocaine cream (EMLA) for topical anaesthesia before vascular access. Br J Anaesth. 2009; 102:210-215.
Sethna, A randomized controlled trial to evaluate S-Caine patch for reducing pain associated with vascular access in children. Anesthesiology. 2005; 102:403-408.

(56) References Cited

OTHER PUBLICATIONS

Singer, Warm lidocaine/tetracaine patch versus placebo before pediatric intravenous cannulation; a randomized controlled trial. Ann Emerg Med. 2008; 52:41-47.
Berman, Self-warming lidocaine/tetracaine patch effectively and safely induces local anesthesia during minor dermatologic procedures. Dermatol Surg. 2005; 31:135-138.
Curry, Use of the Syneral patch for local anesthesia before vascular access procedures: a randomized, double-blind, placebo-controlled study. Pain Med. 2007;8:489-502.
Schecter, Randomized, double-blind, placebo-controlled study evaluating the lidocaine/tetracaine patch for induction of local anesthesia prior to minor dermatologic procedures in geriatric patients. Dermatol Surg. 2005; 31:287-291.
Mehra, Lidocaine toxicity. Anesth Prog. 1998; 45:38-41.
Peers, Patellar tendinopathy in atheletes: current diagnostic and therapeutic recommendations. Sports Medicine. 2005; 35:71-87.
Rees, Current concepts in the management of tendon disorders. Rheumatology (Oxford). 2006; 45:508-521.
Abate, Pathogenesis of tendinopathies: inflammation or degeneration? Arthritis Research and Therapy. 2009; 11:235.
McCarty, Results of controlled study of combination therapy with azathioprine and methotrexate in the treatment of rheumatoid arthritis revisited: comment on the article by Willkens et al. Arthritis Rheum. 1996; 39:1436-1437.
Lian, Pronociceptive and antinociceptive neuromediators in patellar tendinopathy. Am J Sports Med. 2006; 34:1801-1808.
Forsgren, Vascular NK-1 receptor occurrence in normal and chronic painful Achilles and patellar tendons: studies on chemically unfixed as well as fixed specimens. Regul Pept. 2005; 126:173-181.
Jessell, Opiate analgesics inhibit substance P release from rat trigeminal nucleus. Nature. 1977; 268:549-551.
Alfredson, In vivo microdialysis and immunohistochemical analyses of tendon tissue demonstrated high amounts of free glutamate and glutamate NMDAR1 receptors, but no signs of inflammation, in Jumper's knee. J. Orthop Res. 2001; 19:881-886.
Alfredson, Chronic tendon paid: no signs of chemical inflammation but high concentrations of the neurotransmitter glutamate. Implications for treatment? Curr Drug Targets. 2002; 3:43-54.
Scott, VGluT2 expression in painful Achilles and patellar tendinosis: evidence of local glutamate release by tenocytes. J Orthop Res. 2008; 26:685-692.
Magra, VOCCs and TREK-1 ion channel expression in human tenocytes. Am J Physiol Cell Physiol. 2007; 292: C1053-C1060.
Ritchie, On the mode of action of local anesthetics. Annual Review of Pharmacology. 1966; 6:405-430.
Sugimoto, Local anaesthetics have different mechanisms and sites of action at the recombinant N-methyl-Daspartate (NMDA) receptors. British Journal of Pharmacology. 2003; 138:876-882.
Tadicherla, Percutaneous dermal drug delivery for local pain control. Therapeutics and Clinical Risk Management. 2006; 2:99-113.
Visentini, The VISA score: an index of severity of symptoms in patients with jumper's knee (patellar tendinosis). Victorian Institute of Sport Tendon Study Group. Journal of Science and Medicine in Sport. 1998; 1:22-28.
Nishizawa, The inhibition of the N-methyl-D-aspartate receptor channel by local anesthetics in mouse CA1 pyramidal neurons. Anesth Analg. 2002; 94:325-30, table.
Frohm, Patellar tendinopathy—on evaluation methods and rehabilitation techniques. Stockholm: Karolinska University Press; 2006.
Khan, The painful nonruptured tendon: clinical aspects. Clin Sports Med. 2003; 22:711-725.
Khan, Patellar tendinosis (jumper's knee): findings at histopathologic examination, US, and MR imaging. Victorian Institute of Sport Tendon Study Group. Radiology. 1996; 200:821-827.

Astrom, No effect of piroxicam on achilles tendinopathy. A randomized study of 70 patients. Acta Orthop Scand. 1992; 63:631-634.
Khan, Overuse tendon injuries: where does the pain come from? Sports Medicine and Arthroscopy Review. 2000; 8:17-31.
Riley, Tendinopathy—from basic science to treatment. Nature Clinical Practice Rheumatology. 2008; 4:82-89.
Scott, VEGF expression in patellar tendinopathy: a preliminary study. Clin Orthop. 2008; 466:1598-1604.
Astrom, Chronic Achilles tendinopathy. A survey of surgical and histopathologic findings. Clin Orthop. 1995; 151-164.
Danielson, Studies on the importance of sympathetic innervation, adrenergic receptors, and a possible local catecholamine production in the development of patellar tendinopathy (tendinosis) in man. Microscopy Research and Technique. 2007; 70:310-324.
Jensen, Evaluation of eccentric exercise in treatment of patellar tendinitis. Physical Therapy. 1989; 69:211-216.
Cannell, A randomised clinical trial of the efficacy of drop squats or leg extension/leg curl exercises to treat clinically diagnosed jumpers knee in athletes: pilot study. Br J Sports Med. 2001; 35:60-64.
Centini, Suicide due to oral ingestion of lidocaine: a case report and review of the literature. Forensic Science International. 2007; 171:57-62.
U.S. Appl. No. 12/652,502, filed Jan. 5, 2010; Jie Zhang; office action issued Nov. 17, 2011.
Yap, "Myofascial Pain—An Overview"; Ann Acad. Med. Singapore vol. 36, pp. 43-48, 2007.
Hines et al; Use of Lidocaine Patch 5% for Chronic Low Back Pain: A Report of Four Cases; Pain Medicine; Dec. 2002; pp. 361-365; American Academy of Pain Medicine.
Astra USA, Inc., "Elma Cream (lidocaine 2.5% and prilocaine 2.5%)", Product Information Form for American Hospital Formulary Service, 1993, p. 1-28.
Burch et al.; Lidocaine patch 5% improves pain, stiffness, and Physical function in osteoarthritis pain patients, A prospective, multicenter, open-label effectiveness trial; Osteoarthritis and Cartilage; 2004; pp. 253-255; vol. 12; Elsevier Ltd/Osteo Arthritis Research Society International.
Knutson et al., "Solvent-Mediated Alterations of the Stratum Corneum", Journal of Controlled Release vol. 11, 1990, p. 93-103.
Lycka, "EMLA, a New and Effective Topical Anesthetic", J. Dermotol. Surg. Oncol., vol. 18,1992, p. 859-862.
Mack Publishing Company, "Stability of Pharmaceutical Products", Pharmaceutical Sciences, p. 1481-2,1985.
McCafferty et al., Comparative In Vivo and In Vitro Assessment of the Percutaneous Absorption of Local Anaesthetics:, Br. J. Anasth., vol. 60, 1988, p. 64-69.
McCafferty et al., "In Vivo Assessment of Percutaneous Local Anesthetic Preparations", Br. J. Anaesth., vol. 62, 1989, p. 18-21.
McCafferty et al., "New Patch Delivery System for Percutaneous Local Anesthesia", Br. J. Anaesth., vol. 71, 1993, p. 370-374.
Sakamoto et al., "Dermal Patch Anesthesia: Comparison of 10% Lignocaine Gel with Absorption Promoter and Emla Cream", Anesthesia, vol. 48, 1993, p. 390-392.
Woolfson et al., "Concentration Response Analysis of Percutaneous Local Anesthetic Formulations", Br. J. Anaesth., vol. 61, 1988, p. 590-592.
Woolfson, "Percutaneous Local Anesthesia", Formulation of Local Anesthsia for Percutaneous Delivery (Ch. 5), E. Horwood, NY, 1993 p. 166-170.
Radnovich et al.; Utility of the heated lidocaine/tetracaine patch in the treatment of pain associated with shoulder impingement syndrome: a pilot study; International Journal of General Medicine; Jul. 2013:6 641-646; Dove Medical Press Ltd.

\* cited by examiner

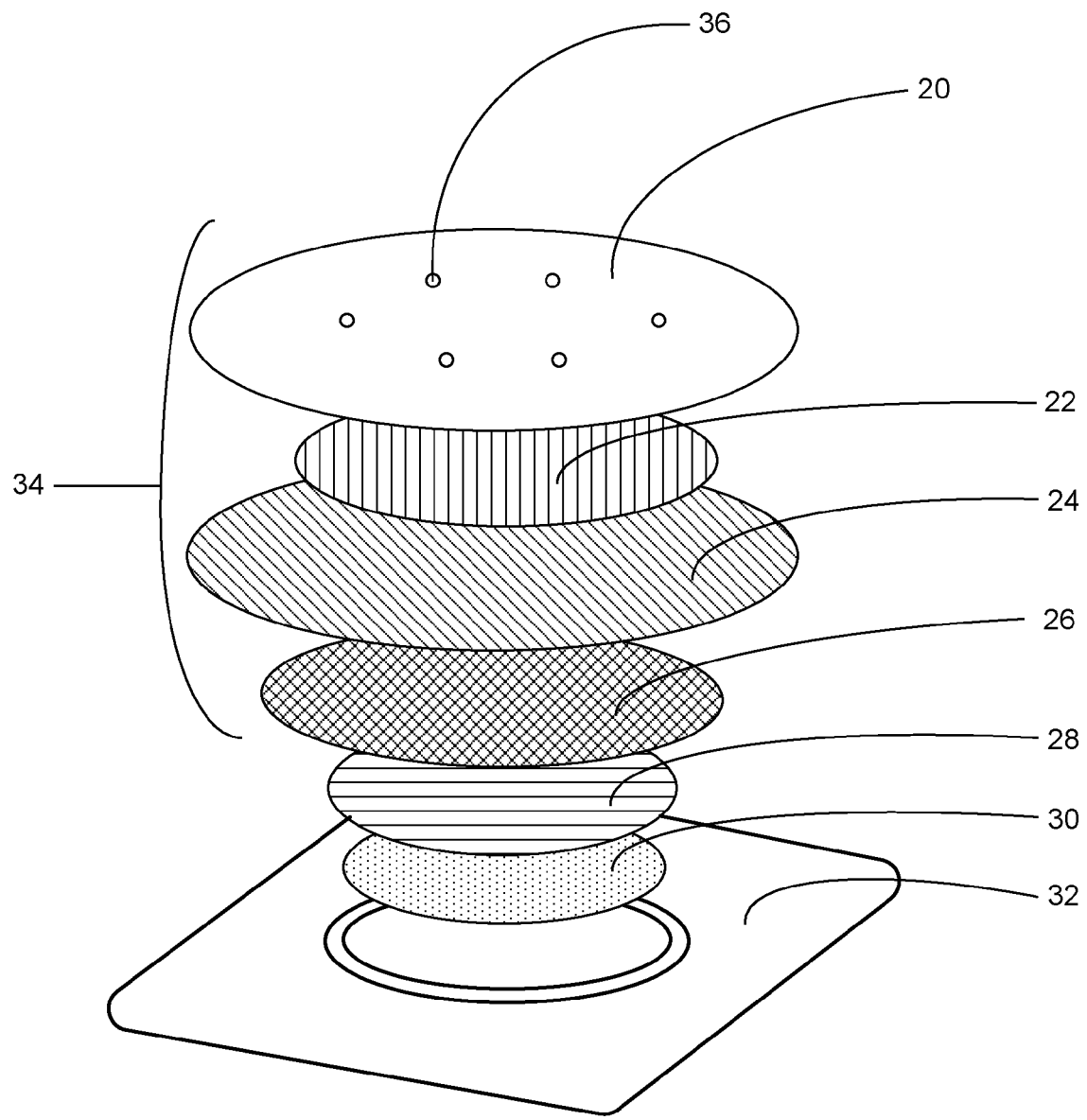

HEAT ASSISTED LIDOCAINE AND TETRACAINE FOR TRANSDERMAL ANALGESIA

This application is a continuation-in-part of U.S. patent application Ser. No. 12/773,239, filed May 4, 2010, which claims the benefit of U.S. Provisional Patent Application No. 61/175,181, filed May 4, 2009, each of which is incorporated herein by reference.

BACKGROUND OF THE INVENTION

Pains associated with nerve conditions afflict many people. Examples of such pain include point pain, nerve entrapment pain (carpal tunnel syndrome, ulnar neuropathy, pudendal nerve entrapment), focal pain, IT band pain, trigger point pain including headaches associated with trigger point pain, occipital neuralgia, arthritis pain, and pain associated with injury or from over use of muscles or joints.

These types of pain are frequently treated with opioid and non-opioid analgesics delivered orally or by injection. Unfortunately, these treatment options suffer from various drawbacks and undesirable side-effects. These undesirable side-effects are frequently due to their systemic delivery. Accordingly, research continues into alternative methods of ameliorating some of these types of regional pain pains.

BRIEF DESCRIPTION OF THE DRAWING

FIG. 1 is a schematic representation of an exemplary analgesic system in the form of a patch which can be used for treating various types of pain.

DETAILED DESCRIPTION

Before particular embodiments of the present invention are disclosed and described, it is to be understood that this invention is not limited to the particular process and materials disclosed herein as such may vary to some degree. It is also to be understood that the terminology used herein is used for the purpose of describing particular embodiments only and is not intended to be limiting, as the scope of the present invention will be defined only by the appended claims and equivalents thereof.

In describing and claiming the present invention, the following terminology will be used.

The singular forms "a," "an," and "the" include plural referents unless the context clearly dictates otherwise. Thus, for example, reference to "a local anesthetic" includes reference to one or more of such compositions.

"Skin" is defined to include human skin (intact, diseased, ulcerous, or broken), and mucosal surfaces that are usually at least partially exposed to air such as lips, genital and anal mucosa, and nasal and oral mucosa.

It is also noted that "local anesthetics" in appropriate formulations can be used to provide skin "anesthesia," which by medical definition means preventing a pain before it happens, such as preventing a pain caused by needle stick. The present disclosure, however, is related to methods of using a local anesthetic formulation to provide "analgesia," which by medical definition means to reduce or eliminate an existing pain, e.g., nerve entrapment pain; neuroma pain; headache associated with neuralgia, such as occipital neuralgia or trigeminal neuralgia; connective tissue pain such as iliotibial band pain, blood vessel pain, tendinopathy pain, medial tibial stress syndrome pain, bursitis, etc.; arthritis pain such as osteoarthritis pain or rheumatoid arthritis pain; pain associated with injury such as fracture, severance, break, sprain, strain, tear, point pain (e.g., trigger point pain or hit point pain), focal pain, or bruise; pain associated with overuse; or combinations of these pains.

The terms "controlled heating" and "controlled heat" are defined herein to include heat application devices that are capable of heating a skin surface to pre-determined narrow temperature range, and optionally, for a predetermined duration. A controlled heating device that can be used in accordance with systems and methods of the present disclosure can be configured to generate heat promptly when activated. Controlled heating can be achieved through special design of the heating component. For example, controlled heating can be achieved through the use of a properly configured heating element(s) including an exothermic chemical composition. Considerations in generating controlled heat with an exothermic heating component include proper ratios and exothermic chemical compositions used, as well as physical constraints put on the exothermic chemical compositions, e.g., limiting air flow or oxygen contact, spatial configuration of individual heating elements, conductivity of materials used with the exothermic chemical composition, etc. In one embodiment, the heating component can provide heat at a temperature greater than body temperature, but less than a temperature that would cause irreversible skin damage, e.g., burn the skin. An exemplary temperature range that can be implemented for use can be from 35° C. to 47° C., or from 36° C. to 42° C. Other desired temperature ranges include from 38° C. to 42° C. or from 36° C. to 40° C. Heating devices are not limited to the presence of exothermic chemical compositions, as any heating device that provides heating within these ranges can be used in accordance with examples of the present disclosure.

"Nerve entrapment" pain in the present disclosure is the same as that commonly used in modern medicine. This type of pain relates to nerves that are under compression or pressure, or are otherwise constricted. Often these ailments are a result of chronic compression of the nerve(s). Such pains include but are not limited to pains associated with carpal tunnel syndrome, ulnar neuropathy, pudendal nerve entrapment, cubital tunnel syndrome, Guyon canal syndrome, posterior interosseous nerve syndrome, supracapular nerve entrapment, lateral femoral cutaneous nerve entrapment, and Tarsal tunnel syndrome.

When referring to pain associated with "neuroma" in the present disclosure, this includes pains associated with neoplastic tumors or nerve injuries, including traumatic neuroma (often as a result of surgery) and Morton's neuroma (a mononeuropathy of the foot).

Headache or pain associated with "occipital neuralgia" in the present disclosure has the same meaning as that defined in modern medicine. Occipital neuralgia causes a distinct type of headache often accompanied by piercing, throbbing, or electric-shock-like chronic pain in the upper neck, back of the head, and behind the ears, usually on one side of the head. Occasionally, pain is experienced in the scalp, forehead, and behind the eyes. The pain is associated with the greater and lesser occipital nerves, from the upper spinal column to the neck, and scalp at the back of the head. The pain can be caused by irritation or injury to the nerves, which can be the result of trauma to the back of the head, pinching of the nerves by overly tight neck muscles, compression of the nerve as it leaves the spine due to osteoarthritis, or tumors or other types of lesions in the neck. Other causes and symptoms are also possible.

The term "connective tissue" as used herein generally refers to connective tissue proper, excluding bone, cartilage and blood. Connective tissue can be areolar (or loose) connective tissue, adipose connective tissue, fibrous (or dense) connective tissue, elastic connective tissue, and reticular connective tissue. Specific examples of connective tissue herein include tendons, ligaments, iliotibial band, blood vessels, etc.

The phrase "iliotibial band pain" in the present disclosure means the pain associated with the Iliotibial syndrome. Inflammation of the iliotibial band, which is a thick band of fibrous tissue that runs down the outside of the leg, causes the pain.

Pain associated "over use" of joints in the present disclosure includes, but is not limited to, bursitis; tendinopathy including tendonosis, tendonitis or "tennis elbow," patellar tendonitis, clavicular tendonitis, medial tibial stress syndrome, focal pain, point pain (e.g., trigger point pain or hit point pain), etc.

Pain associated "damage" or "injury" of joints in the present disclosure includes, but is not limited to, tissue sprains, fractures, tears, and bruises, e.g., hamstring injuries, sprained ankle, hip pointer bruise, etc.

Pain associated with "arthritis" in the present disclosure relates to pain associated with arthritis, including osteoarthritis and rheumatoid arthritis.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein. Furthermore, when using the term "about" in a range, it is understood that the range also includes the exact numerical values of the range. For example, the range "about 36° C. to about 42° C." explicitly includes and provides an additional direct teaching of the range "36° C. to 42° C."

As used herein, a plurality of local anesthetics, compounds, and/or heating mechanisms may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 to 2.0 mm" should be interpreted to include not only the explicitly recited values of about 0.01 mm to about 2.0 mm, but also include individual values and sub-ranges within the indicated range. Thus, included in this numerical range are individual values such as 0.5, 0.7, and 1.5, and sub-ranges such as from 0.5 to 1.7, 0.7 to 1.5, and from 1.0 to 1.5, etc. Furthermore, such an interpretation should apply regardless of the breadth of the range or the characteristics being described. Additionally, it is noted that all percentages are in weight, unless specified otherwise.

With this background in mind, the present disclosure is drawn to methods for treating nerve entrapment pain; neuroma pain; headache associated with neuralgia, such as occipital neuralgia or trigeminal neuralgia; connective tissue pain such as iliotibial band pain, blood vessel pain, tendinopathy pain, medial tibial stress syndrome pain, bursitis, etc.; arthritis pain such as osteoarthritis pain or rheumatoid arthritis pain; pain associated with injury such as fracture, severance, break, sprain, strain, tear, focal pain from injury, point pain from injury (e.g., trigger point pain or hit point pain), or bruise; pain associated with overuse; or combinations of these pains. Specifically, a method for treating the aforementioned pains includes the application of an analgesic system to a skin surface of a subject experiencing the pain and maintaining the analgesic system on the skin surface for an application period of at least 30 minutes, at least 1 hour, or from 30 minutes to 2 hours. The application site can typically be a skin area over the pain, or can be over one or more trigger points. After the application period, the analgesic system can be removed and the subject can continue to experience reduction in their pain for periods of time of 2 hours to 10 hours, or even from 4 to 12 hours. The analgesic system applied to the skin surface can include a heating component and a local anesthetic formulation including at least one local anesthetic. The heating component can be capable of heating the skin surface to a temperature of 35° C. to 47° C. for a sustained period of time within this narrow temperature range.

The methods of the present disclosure can harness the benefits of both increased delivery of the local anesthetic and the therapeutic effect of heating. Furthermore, in some embodiments, the use of heat can actually improve the penetration and benefit of the local anesthetic(s) compared to the use of the same formulation without application of heat. Stated another way, the methods of the present disclosure can provide enhanced transdermal delivery of the local anesthetic(s) through the use of controlled heating, and the added benefit provided by the heat itself. As the skin is heated, the permeability of the skin to the local anesthetics drugs can increase. Additionally, the heating of the skin itself is also believed to reduce the existing pain. Accordingly, the combination of the transdermal delivery of the local anesthetic from the local anesthetic formulation with the heat from the heating component can cause a more efficient, i.e. faster and more effective, reduction in pain than either the drug or the heat alone.

As described above, the analgesic systems used in the methods of the present disclosure can comprise two major components: a controlled heating component and a local anesthetic formulation. The local anesthetic formulation can be incorporated in a patch and can include an amount of the local anesthetic to provide, with the help of the heating component, sufficient transdermal delivery of the local anesthetic for reducing or eliminating existing pain. A sufficient transdermal delivery of the local anesthetic is defined as a rate of delivery that is high enough to reduce the pain intensity (as measured by patient report of pain intensity) in an average patient by at least 20%, and often at least 30% or even 50%, where reduction of pain is determined in the protocol described in Examples 19-22 herein. With some patients and some conditions, complete pain relief can be achieved. The heating device can be configured for application over a transdermal drug patch and a human skin site where the pain originates or at the site where pain is being experienced by the user. Additionally, the heating device can be configured to heat a skin site to which it is applied to a temperature that provides a therapeutic effect, such as from 35° C. to 47° C., or from 36° C. to 42° C. The heating device can further be capable of maintaining the skin within the above temperature range for a period of time of 30 minutes to 2 hours, or from 30 minutes to 1 hour. In some embodiments, the heating device can be cooled down within this time range, or alternatively, the patch can be removed at a prescribed time while the heating device is still providing heat. Either way, once the heat is removed or the patch as a whole is removed, the methods of the present disclosure can provide continued pain relief for a period of hours, e.g., from 2 hours to 10 hours in some embodiments and from 4 hours to 12 hours in other embodiments.

The ability of the methods of embodiments of the present disclosure to provide ongoing or continued reduction of pain even after removal of the analgesic device is a valuable aspect of the present methods. Unlike analgesic systems that require their continued placement to provide ongoing pain reduction, the analgesic systems used in the presently disclosed methods are capable of providing ongoing reduction in pain even after the heating device and the transdermal patch are removed (or quit delivering appreciable amounts of heat/drug). For example, in some embodiments, the analgesic system can be maintained on the skin for an application period of at least 30 minutes, at least 1 hour, from 30 minutes to 2 hours, or from 30 minutes to 1 hour. The duration of the application period can vary depending on a number of factors, including, but not limited to the cause or source of the pain, the location of the pain on the body, etc. The reduction in pain for the patient can occur within 1 hour of application of the analgesic system to the patient's skin surface. In another embodiment, the reduction in pain can occur within 45 minutes of application of the analgesic system. In yet another embodiment, the reduction in pain can occur within 30 minutes of application of the analgesic system.

After the application period, the analgesic system can be removed. Once removed, the patient can continue experiencing reduction in pain for extended periods of time. In one embodiment, reduction in pain can continue for 2 hours to 10 hours following removal of the analgesic system, or from 4 hours to 12 hours following removal of the analgesic system. The ability to continue providing pain relief even after removal of the patch is advantageous in that it facilitates patient compliance. Many patients do not like the feel or look of transdermal patches and may not use them when there is a need to be in public. Additionally, transdermal patches can cause irritation to some patients, particularly those with sensitive skin. Accordingly, the ability to maintain the analgesic system on the skin for a shorter period of time while providing extended pain reduction can be extremely desirable.

Following this period, another system can be applied to the skin of the patient and maintained for a period of time, e.g., as described above, and then removed. As such, in some instances, a system according to the present disclosure is applied to the skin of a subject according to a dosing schedule, where the schedule may be every 2.5 hours, every 3 hours, every four hours, every 5 hours, every 6 hours, every 7 hours, every 8 hours, every 9 hours, every 10 hours, every 11 hours, every 12 hours, every 18 hours, every 24 hours, every 2 days, every 7 days, etc. The duration of each application may, in some instances, be as described above.

As stated, the analgesic systems of the present disclosure can include a local anesthetic formulation and a heating component. The local anesthetic formulation can be designed to transdermally deliver local anesthetic. The local anesthetic can generally be any local anesthetic known in the art, but in accordance with embodiments of the present disclosure, the local anesthetic formulation includes a eutectic mixture of lidocaine base and tetracaine base. Other local anesthetics or drugs can also be present as well. In another embodiment, the local anesthetic formulation can comprise at least 30 wt % of total local anesthetic. In still other embodiments, lower concentrations of local anesthetics can be used, e.g., at least 10 wt % local anesthetic, at least 15 wt % local anesthetic, at least 20 wt % local anesthetic, or at least 25 wt % local anesthetic. That being stated, the weight percentage guidelines described herein may be modified in order to achieve a desired therapeutic effect. When using a eutectic mixture of local anesthetics, such as lidocaine and tetracaine, the total concentration of each local anesthetic can be chosen to provide an appropriate mix of drug stability, long lasting effectiveness, penetration properties (speed and depth of delivery) when applied with heat, etc. For example, a 2:1 to 1:2 (by weight) ratio of a eutectic mixture of lidocaine and tetracaine can be used, and in one embodiment, a 1:1 (by weight) ratio can be used.

The local anesthetic formulation may also include other ingredients and excipients such as polymers, emulsifiers, chemical permeation enhancers, water or other solvents, and preservatives. In one embodiment, the local anesthetic formulation can include a solidification polymer such as polyvinyl alcohol. In another embodiment, the local anesthetic formulation can include an adhesive polymer which can be capable of adhering to skin.

The local anesthetic formulation portion of the analgesic system can have a skin contact area where the local anesthetic formulation contacts the skin surface. The size of the skin contact area can vary depending on the targeted region of the subject's body and the nature of the pain being treated. For example, in certain embodiments, the skin contact area can have an area of 2 $cm^2$ to 200 $cm^2$, 7 $cm^2$ to 150 $cm^2$, 15 $cm^2$ to 150 $cm^2$, or 8 $cm^2$ to 15 $cm^2$. In various other embodiments, other size ranges may be appropriate. For example, the skin contact area can have an area of 3 $cm^2$ to 150 $cm^2$, 5 $cm^2$ to 130 $cm^2$, 6 $cm^2$ to 100 $cm^2$, 7 $cm^2$ to 80 $cm^2$, 8 $cm^2$ to 40 $cm^2$, or 8 to 13 $cm^2$, etc. In one aspect of the disclosure, a layer of adhesive can be coated onto the patch outside the contact area, and/or between the skin and the local anesthetic formulation for affixing the system on the skin.

The heating components of the analgesic systems used in the method of the present disclosure can be configured to raise the temperature of a skin surface to which the analgesic system is applied to a therapeutically effective temperature (for providing heat to the site and/or for providing enhanced drug delivery), e.g., about 35° C. to about 47° C. or about 36° C. to about 42° C. The heating component can further be configured to maintain the temperature of the skin surface in the above range for a period of time of at least 30 minutes, e.g., from 30 minutes to 2 hours, or alternatively, less than 2 hours. In one embodiment, the heating component can be configured to maintain the skin surface in the above described temperature range for a period of at least 60 minutes. In still other embodiments, the heating component can be configured to maintain the skin surface in the above described temperature range for a period of at least 2 hours. Though embodiments of the present disclosure relate to applying the patch to a skin site for 30 minutes to 2 hours or less, longer application times are not precluded, e.g., at least 4 hours, at least 6 hours, at least 8 hours, or at least 12 hours.

In yet another embodiment, the system can be used on a chronic basis (at least once a day for at least 75% of the days in a period of time lasting at least two weeks). In a further embodiment, the system can be used more than once a day. The devices of the present disclosure can also be used for acute pain.

It is noted that regardless of the duration of heating, the analgesic systems used in the methods of the present disclosure can be configured to relieve nerve entrapment pain; neuroma pain; headache associated with neuralgia, such as occipital neuralgia or trigeminal neuralgia; connective tissue pain such as iliotibial band pain, blood vessel pain, tendinopathy pain (tendonosis and/or tendinitis), medial tibial stress syndrome pain, bursitis, etc.; arthritis pain such as osteoarthritis pain or rheumatoid arthritis pain; pain associated with injury such as from tissue fracture, severance, break, sprain, strain, tear, point pain from injury (e.g., trigger point or hit point pain), focal pain from injury, or bruise; pain associated with overuse; or combinations of these pains. These pains can be relieved for a period of time beyond the period of time in which the heating component heats and/or which the analgesic system is maintained on the skin surface. In one embodiment, the methods of the present disclosure can provide relief of existing pain for a period of time of at least 2 hours. In another embodiment, the relief of pain can be for a period of time of at least 4 hours. In another embodiment, the relief of pain can be for a period of time of at least 6 hours. In another embodiment, the relief of pain can be for a period of time of at least 8 hours. In another embodiment, the relief of pain can be for a period of time of at least 10 hours. In another embodiment, the relief of pain can be for a period of time of at least 12 hours. These prolonged time frames for pain relief can often be achieved with transdermal patch application times of less than 2 hours, less than 1 hour, or 30 minutes.

The heating components of the analgesic systems used in the methods of the present disclosure can generate heat through a number of mechanisms or means. In one embodiment, the heating component can generate the heat through chemical-based exothermic reactions. Other heating mechanisms can also be used, such as heating by phase transition of supersaturated solutions (such as phase transition of sodium acetate solutions), radiation (microwave or infrared, for example), electricity-resistor, combinations thereof, and/or other heating sources. In one embodiment, the heating component can be an electric heating device. Such electric heating device can be powered by a variety of sources, for example, battery and/or alternating electric current. Electric devices can be configured to provide a predetermined heating profile so that the heating profile is met automatically after engaging or turning on the electric device, e.g., use of timers, programmed electricity supply, finite batter power, etc. Alternatively, the heating profile can be met merely by providing heat at an appropriate temperature with an instruction to the user to remove the heating device after a specific period of time.

In one embodiment, the heating component can generate heat by an exothermic oxidative chemical reaction. The chemical-based exothermic oxidation reaction can generate heat through the contact of the oxidative material, e.g. iron, with ambient air. U.S. Pat. No. 6,756,053, which is incorporated herein by reference in its entirety, describes examples of exothermic heating components and devices.

The amount of exothermic chemical composition in the heating component can vary from depending on the desired duration of heating and the size of the heating component. It can be beneficial to limit the amount of the exothermic chemical composition in the heating component, as a large amount of exothermic chemical composition can cause the heating component to be excessively large or cumbersome and impractical for use. In one aspect, the heating device can include up to 2 grams of an exothermic chemical composition and can be configured to heat an area of skin greater than about 8 $cm^2$.

In addition to the oxidizable component, the exothermic heating composition can further include activated carbon, salt (such as sodium chloride), and water. In one aspect, a water-retaining substance, such as vermiculite or wood powder, can also be included in the heating component.

Depending on the configuration of the heating device, when stored for extended period of time the exothermic heating components can generate gas (believed to be methane and hydrogen) which can cause the packaging, in which the exothermic heating component is present, to puff up which can cause complications and problems with respect to storage and transportation. It has been discovered that the inclusion of certain amounts of sulfur-containing compounds, or salts thereof, such as elemental sulfur, sulfates, sulfites, sulfides, or thiosulfates, can reduce or eliminate this gas generation problem when included in the packaging.

Water content in the exothermic chemical composition can have an impact on the heating temperature profile of the heating device. The weight ratio of water to the rest of the ingredients in the exothermic heating component can be in the range of about 1:2.6 to about 1:5.0.

In one aspect, the exothermic chemical composition of the heating component can be manufactured in a manner so as to only have access to ambient oxygen through the holes in a cover that is made of air-impermeable material. In this way, the flow rate of oxygen from ambient air into the exothermic chemical composition, which in turn is a factor which can affect the amount and rate of heat generated by the heating component and the temperature of the skin surface on which the analgesic system is applied. Other factors which can influence the temperature and heat generation of the heating component can be the size of the heating component, the amount of the exothermic chemical composition in the heating component, the number and configuration of holes in the heating component's air impermeable cover material, etc.

By way of example, FIG. 1 is a schematic profile of one embodiment of an analgesic system which could be used in accordance with the methods of the present application. The analgesic system includes a heating component 34 and a local anesthetic formulation 30 or drug component. The heating component includes an air-impermeable top cover film 20 having a plurality of holes 36 therein. The analgesic system is typically packaged in an enclosed environment (not shown) so that the heating component does not heat up prematurely. When exposed to ambient air, the holes allow for the passage of the ambient air through the air-impermeable top cover film to the exothermic chemical composition 22. The layer of exothermic chemical composition is disposed between the air-impermeable top cover film and an adhesive film layer 24. The adhesive film layer extends beyond the circumference of the exothermic chemical composition layer and the local anesthetic formulation layer and can function, at least in part, to adhere to the analgesic system to a skin surface. A heat sealable film layer 26 is below to the adhesive film layer and acts to impede the transfer of substances, particularly moisture, between the local anesthetic formulation layer and the exothermic chemical composition layer. Below the heat sealable film layer, a sodium-borate coated non-woven film layer 28 aids in gelling the local anesthetic formulation during manufacturing. The drug component/local anesthetic formulation is adhered in an air and moisture impermeable packing tray 32 which holds the local anesthetic formulation during storage. Thus, the drug component is separated from the heating component within the packaging/enclosed environment, providing a three way separation, e.g., isolation, between the drug component, the heating component, and the outer ambient environment.

When using an appropriate combination of heat and local anesthetics as described herein, the analgesic system can provide fast pain relief (e.g., less than 1 hour), deep penetration (e.g., from about ½ cm to about 1 cm or more of penetration into the body tissues), and long lasting effect (e.g., from 2 hours to 10 hours) after removal of the analgesic systems of the present disclosure.

EXAMPLES

The following examples illustrate embodiments of the disclosure that are presently best known. However, it is to be understood that the following are only exemplary or illustrative of the application of the principles of the present disclosure. Numerous modifications and alternative compositions, methods, and systems may be devised by those skilled in the art without departing from the spirit and scope of the present disclosure. The appended claims are intended to cover such modifications and arrangements. Thus, while the present disclosure has been described above with particularity, the following examples provide further detail in connection with what are presently deemed to be the most practical and preferred embodiments of the disclosure.

Example 1

System for Treating Pain

The analgesic system described herein has two components: a drug component (drug formulation composition in a patch) and a heating component. Table 1 lists exemplary ingredients in the drug component. Table 2 lists exemplary ingredients of the heating component. The drug component of the system in this example has a skin contact area of about 10 $cm^2$, though other sizes may also be prepared.

TABLE 1

| Ingredient | Weight percentage (%) | Weight per patch (mg) | Function |
|---|---|---|---|
| Lidocaine base | 20.00 | 70.0 | Active ingredient |
| Tetracaine base | 20.00 | 70.0 | Active ingredient |
| Polyvinyl alchol (PVA) | 7.20 | 25.2 | Polymeric matrix |
| Sorbitan monopalmitate (Span 40) | 3.00 | 10.5 | Emulsifying agent |
| Purified Water | 49.68 | 173.88 | Solvent |
| Methyl parahydroxybenzoate | 0.10 | 0.35 | Preservative |
| Propylparagydroxybenzoate | 0.02 | 0.07 | Preservative |

*Sodium-borate coated nonwoven film at 10.84 $cm^2$ was used, which gelled the drug formulation

TABLE 2

| COMPONENT | Weight Percentage (%) | Weight Per Patch (grams) |
|---|---|---|
| Iron Powder Activated Carbon | 50 | 0.80 |
| Activated Carbon | 15.63 | 0.25 |
| Sodium Chloride | 6.25 | 0.10 |
| Wood Flour | 9.38 | 0.15 |
| Water | 18.74 | 0.3 |

The physical configurations of the drug component and the heating component, and their integration, are schematically shown in FIG. 1. The heat generating medium is enclosed in a closed space as shown in FIG. 1, and is accessible to the external environment only through the 6 holes on the air-impermeable cover. The diameter of each of the holes is about 1/16 of an inch. This heat generating medium can provide controlled heat at from 36 to 42° C. for a sustained period of time.

Example 2

System for Treating Pain

Four small analgesic systems described in Example 1 are prepared, except that the size of the patches are varied to have a skin contact area of 2 $cm^2$, 3 $cm^2$, 6 $cm^2$, and 8 $cm^2$, respectively. Thus, the weight percentages are the same for both the drug formulation (Table 1) and the heat generating medium (Table 2), but since the patches are smaller in size, the total amount of each ingredient is proportionally reduced. The number of holes or the size of the holes is also modified so that the total hole area (number of holes times the surface area of each hole) is adjusted proportionally in order to achieve a similar heating profile for the patch size, e.g., 1-6 holes of similar or slightly different size.

Example 3

System for Treating Pain

Four large analgesic systems described in Example 1 are prepared, except that the size of the patches are varied to have a skin contact area of 40 $cm^2$, 60 $cm^2$, 120 $cm^2$, 180 $cm^2$, respectively. Thus, the weight percentages are the same for both the drug formulation (Table 1) and the heat generating medium (Table 2), but since the patches are much larger in size, the total amount of each ingredient is proportionally increased. The number of holes or the size of the holes is also adjusted proportionally in order to achieve a similar heating profile for the patch size. The number of holes or the size of the holes is also modified so that the total hole area (number of holes times the surface area of each hole) is adjusted proportionally in order to achieve a similar heating profile for the patch size, e.g., 12-100 holes of similar or slightly different size.

Example 4

System for Treating Pain

An analgesic systems described in Example 1 is prepared, except that the heat generating medium is from an electric heating device, and the patch size is modified to 120 $cm^2$. Thus, the weight percentage is the same for the drug formulation (Table 1), but since the patch is larger in size, the total amount of each ingredient is proportionally increased.

Example 5

Treating Headache-Occipital Neuralgia

A patient is suffering from severe headache and is diagnosed as occipital neuralgia. After taking multiple oral medications, including opioids, to control the headache pain, an analgesic system similar to that described in Example 1 is applied to the neck twice daily, which reduces the pain and enables the patient to discontinue the oral pain medications. The analgesic system can be applied at from 30 minutes to 2 hours, and the pain relief can last from 2-10 hours after removal, or even from 4-12 hours after removal.

Example 6

Treating Neuroma

A patient with ACL tear and knee arthroscopy surgery experiencing pain due to surgically induced neuroma is treated with an analgesic system similar to that in Example 1. The analgesic system is applied to either side of the knee (2 total patches). Pain relief is obtained 30 minute following the application and can last 2-10 hours, or even 4-12 hours after removal of the analgesic system.

Example 7

Treating Nerve Entrapment

A patient with carpal tunnel syndrome experiencing pain is treated with an analgesic system similar to that in Example 1. The analgesic system is applied to the wrist of the patient. Pain relief is obtained 30 minute following the application and can last 2-10 hours, or even 4-12 hours after removal of the analgesic system.

Example 8

Treating Focal Foot Pain

A patient is suffering focal foot pain due to repetitive use as a ballerina. A system similar to that in Example 1 is applied on the skin over the pain area. Pain relief is achieved following a 30 minute application and lasts over eight hours. This analgesic system can be desirable over other topical treatments because it can be removed after 30 minutes and have continuous pain relief for a period of hours. This is useful when the patient prefers not to have an unsightly patch showing on the foot. For example, the analgesic system can be applied at from 30 minutes to 2 hours, and the pain relief can last from 2-10 hours after removal, or even from 4-12 hours after removal.

Example 9

Treating Severe Occipital Neuralgia

A patient is suffering from headaches and is diagnosed with severe occipital neuralgia. Two analgesic systems similar to that described in Example 3 (40 cm$^2$) are applied to the skin over the neck muscles twice daily, which reduces the pain and enables the patient to discontinue the oral pain medications. Alternatively, two analgesic systems are applied to each of the patient's temple twice daily. Combinations of placement locations can also be practiced to achieve maximum pain relief. The analgesic system can be applied at from 30 minutes to 2 hours, a and the pain relief can last from 2-10 hours after removal, or even from 4-12 hours after removal.

Example 10

Treating Connective Tissue Pain

A patient is suffering from connective tissue pain in the shoulder. An analgesic system similar to that described in Example 1 is applied directly to the shoulder area twice daily, which reduces the pain. The analgesic system can be applied at from 30 minutes to 2 hours, and the pain relief can last from 2-10 hours after removal, or even from 4-12 hours after removal.

Example 11

Treating Osteoarthritis Arthritis Pain

A patient is suffering from pain associated with osteoarthritis in both of the knees. An analgesic system similar to that described in Example 3 (120 cm$^2$) is applied to each of the knee for two hours twice daily (every 12 hours), which reduces the pain significantly, even during hours in between application of the analgesic system. The analgesic system can be applied at from 30 minutes to 2 hours, and the pain relief can last from 2-10 hours after removal, or even from 4-12 hours after removal.

Example 12

Treating Rheumatoid Arthritis Pain

A patient is suffering from pain associated with rheumatoid arthritis in both of the knees. An analgesic system similar to that described in Example 3 (120 cm$^2$) is applied to each of the knee for one hour twice daily (every 12 hours), which reduces the pain significantly, even during hours in between application of the analgesic system. The analgesic system can be applied at from 30 minutes to 2 hours, and the pain relief can last from 2-10 hours after removal, or even from 4-12 hours after removal.

Example 13

Treating Pain Associated with Sprained Ankle

A basketball player sprains an ankle during playing basketball and is suffering from the pain associated with the injury. An analgesic system similar to that described in Example 3 (40 cm$^2$) is applied to the ankle for one hour twice daily (every 12 hours), which reduces the pain significantly, even during hours in between application of the analgesic system. The analgesic system can be applied at from 30 minutes to 2 hours, and the pain relief can last from 2-10 hours after removal, or even from 4-12 hours after removal.

Example 14

Treating Pain Associated with Fractured Bone

A football player slightly fractures the collar bone during practice and is suffering from the pain associated with the injury. An analgesic system similar to that described in Example 3 (60 cm$^2$) is applied to skin area over the fracture for one hour twice daily (every 12 hours), which reduces the pain significantly, even during hours in between application of the analgesic system, e.g., from 2-10 hours or from 4-12 hours.

Example 15

Treating Pain Associated with Dislocated Joint

A football player dislocates the right shoulder joint during practice. The dislocation was treated by a doctor but the patient is still suffering from the pain associated with the injury. An analgesic system similar to that described in Example 3 (120 cm$^2$) is applied to shoulder area for one hour twice daily (every 12 hours), which reduces the pain significantly, even during hours in between application of the analgesic system. The pain relief can last from 2-10 hours, or even 4-12 hours after removal.

Example 16

Treating Pain Associated with Dislocated Joint

A sprinter injures his hamstring tendon during practice and is suffering from the pain associated with injury. An analgesic system similar to that described in Example 3 (180 cm²) is applied to skin area over the pain for two hours twice daily (every 12 hours), which reduces the pain significantly, even during hours in between application of the analgesic system. The pain relief can last from 2-10 hours, or even 4-12 hours after removal.

Example 17

Treating Nerve Entrapment

A patient with carpal tunnel syndrome experiencing pain is treated with an analgesic system similar to that in Example 2 (3 cm²). The analgesic system is applied to the wrist of the patient. Pain relief is obtained 30 minute following the application and can last from 2-10 hours, or even 4-12 hours after removal.

Example 18

Treating Pain Associated with Iliotibial Band Pain

A marathon runner is suffering from iliotibial band pain before a race and is expected to have more pain during the running if not treated. An analgesic system similar to that described in Example 3 (180 cm²) is applied to skin area over the pain for one hour and is removed before the running starts. The pain is significantly reduced before the running starts and is much less intense during the running. The pain relief can last from 2-10 hours, or even 4-12 hours after removal.

Example 19

Treating Carpal Tunnel Syndrome

A study was conducted to investigate the effectiveness of an analgesic system, such as the one described in Example 1, in providing pain relief to a subject experiencing mild to moderate carpal tunnel syndrome. Twenty (20) patients were enrolled in the study with 5 of the patients dropping out prior to completion of the study (5 dropouts: 2 for noncompliance, 2 for lack of efficacy, and 1 adverse event, i.e. application site rash). The study was a single site, open label study. The patients in the study applied the analgesic system directly to the painful wrist region that overlies the carpal tunnel for 2 hours twice daily (morning and evening, approximately 12 hours apart) for 14 days. No other CTS pain medications were allowed.

In the study, a Visual Analog Scale (VAS) of pain intensity (average and worst pain over the last 24 hours and pain now) and pain interference with general activity, normal work, and sleep were considered. The scales used were the subject Global Assessment of Treatment Satisfaction (5-point scale), and the subject and investigator Clinical Global Impression of Improvement (7-point scale).

The VAS scores for average pain, worst pain, and pain now decreased in all categories, as shown below in Table 3 (negative % indicating decrease in pain). Also shown in Table 3 is a reduction in pain interference with general activity, normal work, and sleep (negative % indicating reduction in pain interference). It is also noteworthy that most subjects (75%) were satisfied or very satisfied with their treatment and 55% were much improved or very much improved based on the global impression of improvement by both the subjects and investigator.

TABLE 3

| Measure | ITT Population (n = 20) | Per Protocol Population (n = 15) |
|---|---|---|
| Pain Intensity | | |
| Average Pain | −37% | −52% |
| Worst Pain | −41% | −55% |
| Pain Now | −34% | −50% |
| Pain Interference with Activity | | |
| General Activity | −49% | −62% |
| Normal Work | −47% | −64% |
| Sleep | −58% | −80% |

As can be seen by this study, the application of the analgesic system of the present disclosure directly over the site of pain associated with carpal tunnel syndrome was effective in reducing pain intensity and decreasing pain interference with activities of daily living, especially sleep. Further, it is noteworthy that the patients had meaningful reductions in pain across all pain measures even after the removal of the analgesic system.

Example 20

Treating Shoulder Impingement

A study was conducted to investigate the effectiveness of an analgesic system, such as the one described in Example 1, in providing pain relief to subjects experiencing VAS pain scores values of ≥4 in one shoulder. Twenty (20) patients were enrolled in the study with 1 of the patients dropping out prior to completion of the study (lost to follow up). The study was a single site, open label study in which the patients in the study applied the analgesic system to the skin surface proximate to the source of the shoulder impingement pain twice daily BID (once every 12 hours) for 14 consecutive days. The analgesic system was maintained on the skin for a period of 2-4 hours before being removed.

In the study, a Visual Analog Scale (VAS) of pain intensity (average and worst pain over the last 24 hours) and pain interference with general activity, normal work, and sleep were considered. The scales used were the subject Global Assessment of Treatment Satisfaction (5-point scale), and the subject and investigator Clinical Global Impression of Improvement (7-point scale).

The VAS scores for average pain and worst pain decreased for both categories, as shown below in Table 4 (negative % indicating decrease in pain). Also shown in Table 4 is a reduction in pain interference with general activity, normal work, and sleep (negative % indicating reduction in pain interference). Furthermore, in this particular study, increases in range of motion of the shoulder were also observed (positive % indicating improved range of motion).

TABLE 4

| Measure | Population (n = 19) |
|---|---|
| Pain Intensity | |
| Average Pain | −41% |
| Worst Pain | −43% |
| Pain Interference with Activity | |
| General Activity | −40% |
| Normal Work | −37% |
| Sleep | −46% |

TABLE 4-continued

| Measure | Population (n = 19) |
|---|---|
| Changes in Range of Motion of Shoulder | |
| Internal rotation | +119% |
| Abduction | +47% |

As can be seen from the results in Table 4, the analgesic system was effective in providing pain reduction for the patients, both in terms of pain intensity and reduction in pain interference. Positive changes in range of motion were observed. Further, it is noteworthy that the patients had meaningful reductions in pain even after the removal of the analgesic system.

Example 21

Treating Myofascial Trigger Point Pain

A study was conducted to investigate the effectiveness of an analgesic system, such as the one described in Example 1, in providing pain relief to subjects experiencing VAS pain scores values of ≥4 for a minimum of a one (1) month and with myofascial trigger point pain. Twenty (20) patients were enrolled in the study with 16 subjects completing the study, 3 dropping out and 1 ongoing. The study was a single site, open label study in which the patients in the study applied the analgesic system to the skin surface proximate the source of the shoulder impingement pain twice daily BID (once every 12 hours) for 14 consecutive days with a day 28 follow-up visit. The analgesic system was maintained on the skin for a period of 4 hours before being removed.

In the study, a Visual Analog Scale (VAS) of pain intensity (average and worst pain over the last 24 hours) and pain interference with general activity, normal work, and sleep were considered. The scales used were the subject Global Assessment of Treatment Satisfaction (5-point scale), and the subject and investigator Clinical Global Impression of Improvement (7-point scale).

The VAS scores for average pain improvement is shown below in Table 5 (negative % indicating decrease in pain). Also shown in Table 5 is a reduction in pain interference with general activity, mood, enjoyment of life, normal work, and sleep (negative % indicating reduction in pain interference).

TABLE 5

| Measure | Population (n = 19) |
|---|---|
| Pain Intensity | |
| Average Pain | −32%* |
| Pain Interference with Activity | |
| General Activity | −46% |
| Mood | −55% |
| Enjoyment of life | −59% |
| Normal work | −42% |
| Sleep | −46% |

*11 of 19 had ≥2 point decrease in average pain

As can be seen from the results in Table 5, the analgesic system was effective in providing pain reduction for the patients, both with respect to pain intensity and reduction of pain interference. Further, it is noteworthy that the patients experienced meaningful reductions in pain across all pain measures even after the removal of the analgesic system.

Example 22

Treating Patellar Tendinopathy Pain

A study was conducted to investigate the effectiveness of an analgesic system, such as the one described in Example 1, in providing pain relief to subjects experiencing VAS pain scores values of ≥4 due to patellar tendinopathy for a minimum of two weeks. Eight (8) patients were enrolled in the study with seven (7) subjects completing the study. The study was a single site, open label study in which the patients in the study applied the analgesic system to the skin surface proximate the source of the tenderness at the proximal insertion of the patellar tendon twice daily BID (once every 12 hours) for 14 consecutive days with a day 28 follow-up visit. The analgesic system was maintained on the skin for a period of 2-4 hours before being removed. The study indicated that the analgesic system was effective in providing pain reduction for the patients including meaningful reductions in pain even after the removal of the analgesic system.

Example 23

Application Time PK Study of Lidocaine and Impact of Tetracaine on Sustained Pain Relief A study was conducted to evaluate the pharmokinetics (PK) of lidocaine and tetracaine when applied to a skin site using controlled heat in accordance with examples of the present disclosure. Specifically, a single site, open label study was conducted on 12 subjects, with 4-way cross-over. Four (4) patches were applied for 2, 4, or 12 hours. The area under the concentration-time curve ($AUC_{0-t}$) for lidocaine doubled as application time increased from 2 hours to 4 hours. Further, lidocaine delivered more rapidly when applied with a heated patch of the present disclosure than with an unheated patch.

Tetracaine, on the other hand, is difficult to evaluate in terms of pharmokinetics because it is less stable than lidocaine in the body. However, it has been discovered that sustained or long lasting pain relief can be achieved (even after removal of the analgesic system of the present disclosure) using a eutectic mixture of lidocaine and tetracaine.

It is noted in the above examples that various skin contact areas, analgesic system contact times, methods of treating specific conditions, etc., are provided for exemplary purposes only. Thus, while the invention has been described with reference to certain embodiments, those skilled in the art will appreciate that various modifications, changes, omissions, and substitutions can be made without departing from the spirit of the invention. It is therefore intended that the invention be limited only by the scope of the appended claims.

What is claimed is:

1. A method for treating an existing pain selected from the group consisting of nerve entrapment pain, neuroma pain, headache pain, connective tissue pain, arthritis pain, pain associated with injury, pain associated with overuse, and combinations thereof, comprising:
   a) applying at least one integrated analgesic system to a skin surface of a subject experiencing pain, said analgesic system comprising:
      i) a heating device configured to heat the skin surface to a temperature of 35° C. to 47° C., and
      ii) a local anesthetic formulation including a eutectic mixture of lidocaine and tetracaine, wherein the local anesthetic formulation is applied to the skin surface over the existing pain;

b) heating the skin surface to a temperature of 35° C. to 47° C.; and c) maintaining the analgesic system on the skin surface for an application period of at least 2 hours.

2. The method of claim 1, wherein the eutectic mixture comprises at least 30 wt % of the local anesthetic formulation.

3. The method of claim 1, wherein the eutectic mixture comprises at least 10 wt % of the local anesthetic formulation.

4. The method of claim 1, wherein the local anesthetic formulation has a skin contact area having an area of 2 cm² to 200 cm².

5. The method of claim 1, wherein the local anesthetic formulation has a skin contact area from 5 cm² to 130 cm².

6. The method of claim 1, wherein the local anesthetic formulation has a skin contact area from 8 cm² to 40 cm².

7. The method of claim 1, wherein the existing pain is an acute pain.

8. The method of claim 1, wherein the subject begins experiencing a reduction of existing pain within 1 hour of application of the analgesic system.

9. The method of claim 1, wherein the subject begins experiencing a reduction of existing pain within 30 minutes of application of the analgesic system.

10. The method of claim 1, wherein two or more analgesic systems are applied to a skin surface of a subject experiencing pain.

11. The method of claim 1, wherein the analgesic system is applied more than once a day.

12. The method of claim 1, wherein the analgesic system is applied as daily treatment for at least two weeks.

13. The method of claim 1, wherein the delivery of the local anesthetic formulation through the skin is more rapid than delivery of the local anesthetic formulation using an unheated patch.

14. The method of claim 1, wherein the reduction of pain includes a reduction in pain intensity and pain interference.

15. The method of claim 1, wherein the existing pain is pain associated with at least one of the head, neck, shoulder, knee, leg, ankle, hip, elbow or wrist.

16. The method of claim 1, wherein the eutectic mixture of lidocaine and tetracaine is at a weight ratio of 2:1 to 1:2.

17. The method of claim 1, wherein the heating device is configured to generate heat by an exothermic oxidative chemical reaction.

18. The method of claim 1, wherein the skin surface is heated to a temperature of 36° C. to 42° C.

19. The method of claim 1, wherein the skin surface is heated to a temperature of 38° C. to 42° C.

20. The method of claim 1, wherein the skin surface is heated to a temperature of 36° C. to 40° C.

21. The method of claim 1, further comprising removing the analgesic system after the application period, wherein the subject experiences a reduction of pain during at least a portion of the application period and for a period of 2 hours to 10 hours after removal of the analgesic system.

22. The method of claim 1, wherein the existing pain is the nerve entrapment pain.

23. The method of claim 22, wherein the nerve entrapment pain is associated with carpal tunnel syndrome, ulnar neuropathy, pudendal nerve entrapment, cubital tunnel syndrome, Guyon canal syndrome, posterior interosseous nerve syndrome, supracapular nerve entrapment, lateral femoral cutaneous nerve entrapment, or Tarsal tunnel syndrome.

24. The method of claim 1, wherein the existing pain is the neuroma pain.

25. The method of claim 1, wherein the neuroma pain is associated with a neoplastic tumor, nerve injury, traumatic neuroma, or Morton's neuroma.

26. The method of claim 1, wherein the existing pain is the headache pain.

27. The method of claim 26, wherein the headache pain is associated with occipital neuralgia.

28. The method of claim 1, wherein the existing pain is the connective tissue pain.

29. The method of claim 28, wherein the connective tissue pain is associated with areolar connective tissue, adipose connective tissue, fibrous connective tissue, elastic connective tissue, reticular connective tissue, a tendon, a ligament, an iliotibial band, or a blood vessel.

30. The method of claim 1, wherein the existing pain is the arthritis pain.

31. The method of claim 30, wherein the arthritis pain is osteoarthritis pain or rheumatoid arthritis pain.

32. The method of claim 1, wherein the existing pain is pain associated with injury.

33. The method of claim 32, wherein the injury is a fracture, a severance, a break, a sprain, a strain, a tear, a point pain, a focal pain, or a bruise.

34. The method of claim 1, wherein the existing pain is pain associated with overuse.

35. The method of claim 34, wherein the overuse is related to tendonosis, tendonitis, patellar tendonitis, clavicular tendonitis, medial tibial stress syndrome, focal pain, point pain, or muscle pain.

* * * * *